United States Patent [19]

Baggiolini et al.

[11] 4,225,525
[45] Sep. 30, 1980

[54] VITAMIN D₃ METABOLITE DERIVATIVES

[75] Inventors: Enrico G. Baggiolini, Bloomfield; Milan R. Uskokovic, Upper Montclair, both of N.J.

[73] Assignee: Hoffmann-La Roche Inc., Nutley, N.J.

[21] Appl. No.: 10,448

[22] Filed: Feb. 8, 1979

[51] Int. Cl.³ ............................................. C07J 9/00
[52] U.S. Cl. ................................. 260/397.2; 424/213
[58] Field of Search ..................................... 260/397.2

[56] References Cited

U.S. PATENT DOCUMENTS

| | | | |
|---|---|---|---|
| 3,657,279 | 4/1972 | Higashi et al. | 260/397.2 |
| 3,993,675 | 11/1976 | Uskokovic et al. | 260/397.2 |
| 4,098,801 | 7/1978 | Micheli | 260/397.2 |

FOREIGN PATENT DOCUMENTS 2837414  3/1979  Fed. Rep. of Germany ........ 260/397.2

OTHER PUBLICATIONS

Gemeiner, "Chem. Abst. (1976) vol. 85, Par. 89628(m).

Primary Examiner—Elbert L. Roberts
Attorney, Agent, or Firm—Jon S. Saxe; George M. Gould; James H. Callwood

[57] ABSTRACT

This disclosure relates to 3-hemisuccinate or 3-hemiglutarate derivatives of the biologically active metabolites of Vitamin D₃ which possess Vitamin D activities and uses. The subject compounds also are useful as haptens which can be used to prepare immunogens which in turn elicit antibodies selective to said respective Vitamin D₃ metabolites.

6 Claims, No Drawings

VITAMIN D₃ METABOLITE DERIVATIVES

BACKGROUND OF THE INVENTION

The hemisuccinate of cholesterol is described in Example 2 of U.S. Pat. No. 3,657,279. No utility for this compound is disclosed.

U.S. Pat. No. 3,936,478 discloses the use of divalent protective groups including dicarboxylic acid esters such as succinate or glutarate esters to protect the 3-hydroxy group of 24-hydroxycholesterol during dehydration to desmosterol. The divalent protecting groups result in the formation of dimeric compounds.

U.S. patent application Ser. No. 867,204, filed Jan. 5, 1978, inventors Fairney et al, title "1α,25-Dihydroxycholecalciferol Assay" describes the preparation 1α-hydroxycholecalciferol-25-hydroxy-hemisuccinate which is utilized as a hapten in the preparation of an antigen which can elicit antibodies selective to 1α,25-dihydroxycholecalciferol. These antibodies are then used in an immunoassay for this important therapeutic substance. No Vitamin D-like activity, or for that matter, any biological activity is ascribed to the 25-hemisuccinate derivative.

The 3-hemisuccinate of Vitamin D₃ (cholecalciferol) is disclosed by Gemliner, Chem. Abstracts 85:89628m (1976). This compound is utilized as a hapten for the same general purpose (immunoassay) as described immediately above. No biological activity is ascribed to the hemisuccinate derivative.

DESCRIPTION OF THE INVENTION

The present invention relates to novel derivatives of Vitamin D₃ metabolites, methods for their preparation, and novel intermediates useful in said production. More particularly, the invention relates to novel Vitamin D₃ metabolite derivatives of the formula:

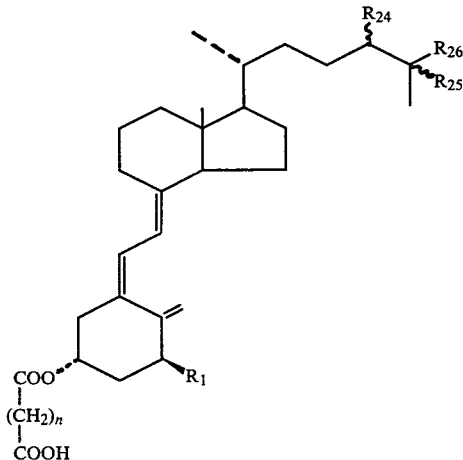

where $R_1$, $R_{24}$, $R_{25}$ and $R_{26}$ each independently are hydrogen hydroxy or fluorine, provided that at least one of $R_1$, $R_{24}$, $R_{25}$, $R_{26}$ is hydroxy, n is an integer selected from 2 or 3, and base salts thereof.

Representative compounds of formula I include the following:

1α,25-dihydroxycholecalciferol-3-hemisuccinate
1α,24,25-trihydroxycholecalciferol-3-hemisuccinate
24,25-dihydroxycholecalciferol-3-hemisuccinate
1α-hydroxycholecalciferol-3-hemisuccinate
24-hydroxycholecalciferol-3-hemisuccinate
25-hydroxycholecalciferol-3-hemisuccinate
1α,25-dihydroxycholecalciferol-3-hemiglutarate
1α,24,25-trihydroxycholecalciferol-3-hemiglutarate
24,25-dihydroxycholecalciferol-3-hemiglutarate
1α-hydroxycholecalciferol-3-hemiglutarate
24-hydroxycholecalciferol-3-hemiglutarate
25-hydroxycholecalciferol-3-hemiglutarate
25,26-dihydroxycholecalciferol-3-hemiglutarate
1α,24-dihydroxycholecalciferol-3-hemisuccinate
1α,24-dihydroxycholecalciferol-3-hemiglutarate
1α,24-dihydroxy-25-fluoro-cholecalciferol-3-hemisuccinate
1α,25,26-trihydroxycholecalciferol-3-hemisuccinate
1α,25,26-trihydroxycholecalciferol-3-hemiglutarate Preferred compounds of the invention are obtained when n is 2, i.e., the hemisuccinates. A most preferred compound is 1α,25-dihydroxycholecalciferol 3-hemisuccinate.

Compounds of formula I, having a free carboxyl group can be obtained in the form of their pharmaceutically acceptable base salts. Suitable base salts include the alkali metals particularly sodium and potassium alkaline earth metals, ammonium and organic bases such as guanidine, triethylamine, ethanolamine, aminoethylglucine and the like.

Compounds of formula I are readily prepared starting from the known 7-dehydrocholesterol compound of the following formula

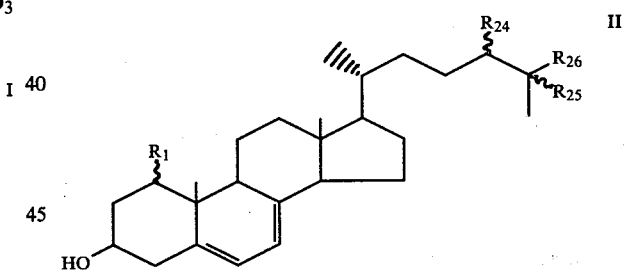

where $R_1$, $R_{24}$, $R_{25}$ and $R_{26}$ taken independently are as above and any two of $R_{24}$, $R_{25}$ and $R_{26}$ taken together are hydroxys protected as the acetonide.

In the first step of the process aspect of the present invention a compound of formula II is reacted with a compound of the formula

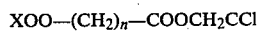

$$XOO-(CH_2)_n-COOCH_2CCl \qquad III$$

where X is bromo or chloro, preferably chloro and n is as above in a cyclic ether solvent such as tetrahydrofuran and an organic nitrogen acid acceptor compound such as pyridine, preferably in a mixture of pyridine and tetrahydrofuran under anhydrous conditions and an inert atmosphere, such as argon or nitrogen, at a temperature in the range of about −10° to 30° C. so as to produce a compound of the formula:

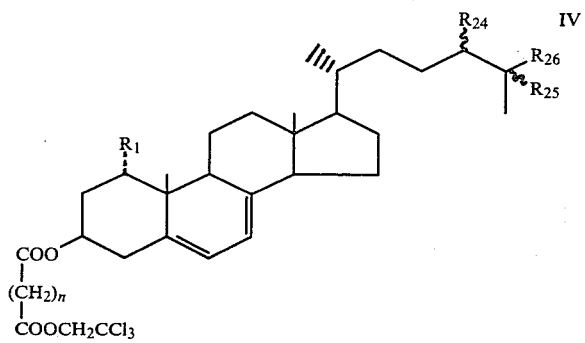

where n, $R_1$, $R_{24}$, $R_{25}$ and $R_{26}$ are as above.

In the next process step, the compound of claim IV is irradiated with ultraviolet light from a high pressure lamp source emitting in the range from 250 to 300 nm in a manner known per se so as to produce a precholecalciferol compound of the formula:

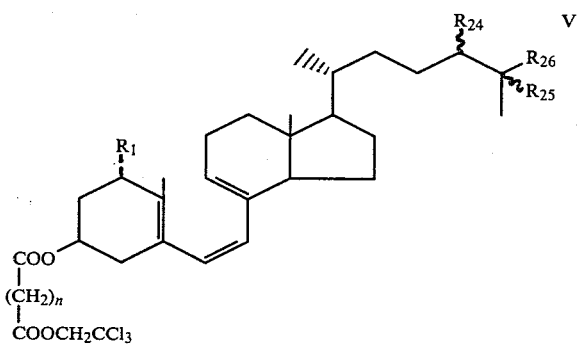

where n, $R_1$, $R_{24}$, $R_{25}$ and $R_{26}$ are as above.

The irradiation procedure is conveniently carried out in an inert solvent medium, preferably a liquid alkane such as pentane, n-hexane, n-heptane or the like, or a cyclic ether solvent such as tetrahydrofuran or preferably mixtures thereof. A temperature the range of from about −10° to 10° C., preferably at about 0° C. is employed.

The reaction medium, after irradiation, usually contains a mixture of starting material and final product. These products can be separated by using conventional chromatographic technique high pressure liquid chromatography is preferred.

The compound of formula V is then thermally isomerized by heating under anhydrous conditions and preferably under an inert atmosphere utilizing a suitable inert organic solvent such as a cyclic ether preferably dioxane so as to produce a cholecalciferol compound of the formula

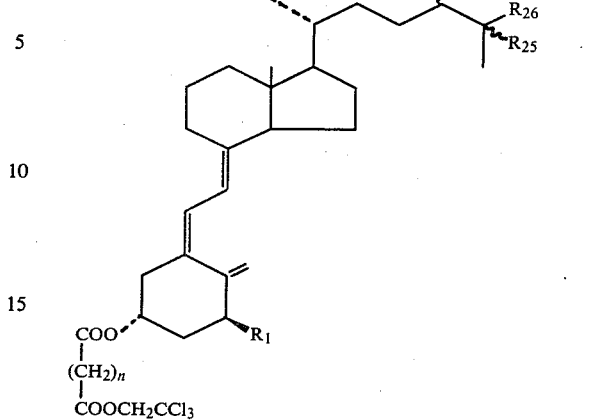

where n, $R_1$, $R_{24}$, $R_{25}$ and $R_{26}$ are as above.

In the next process step, the compound of formula VI is treated with zinc powder at a temperature in the range of about −5° to 20° C., preferably at about 0° C. The reaction is carried out in an aqueous organic solvent medium, preferably a cyclic ether.

The resulting product of this reaction step will be the desired products of formula I except where any two vicinal hydroxy groups at positions 24, 25 and/or 26 in the starting compounds of formula II are protected as the acetonide. In the latter circumstance the product of the aforesaid reaction step must be deprotected by treating the acetonide protected reaction product with an acidic agent, preferably an ionic exchange resin in the hydrogen form in a non-aqueous polar solvent such as a $C_{1-3}$ lower alkanol, preferably methanol. An inert atmosphere and light exclusion are emloyed during this reaction to minimize decomposition. The reaction conveniently is carried out at a temperature in the range of from about −5° to 30° C., preferably at about room temperature.

Compounds which are prepared in accordance with this optional deprotection step include the 3-hemisuccinates and 3-hemiglutarates of 24,25-dihydroxy-, 1,24,25-trihydroxy, 25,26-dihydroxy- and 1,25,26-trihydroxy-cholecalciferols.

In a further process embodiment, 24,25-dihydroxy-, 1α,24,25-trihydroxy-, 25,26-dihydroxy- and 1α,25,26-trihydroxy-cholecalciferol, in the form of their respective acetonides, can be treated with succinic anhydride or glutaric anhydride in an inert organic solvent such as pyridine at elevated temperatures, i.e., about 80° C., most preferably at about 100° C. in an inert atmosphere and with the exclusion of light. The resulting respective 3-hemisuccinate or 3-hemiglutarate may be deprotected with an acidic agent in analogy to the procedures described immediately above.

The end products of the invention, i.e., the compounds of formula I, are useful as vitamin and nutritional factors in humans and all species in the veterinarian field and are useful in place of and in combination with the corresponding Vitamin $D_3$ metabolites in the vitamin and nutritional treatment of birds, mammals and man.

Compounds of formula I are particularly useful in treating conditions characterized by low serum levels of Vitamin $D_3$ metabolites, especially where those low levels result from an inability or an impaired ability to convert Vitamin $D_3$ to its biologically active metabolites. These conditions include among others, chronic renal disease, Vitamin D resistant rickets, corticoid-induced decrease in calcium absorption, osteoporosis, senile decrease in calcium absorption, hyperthyroidism, alcholism and the like.

The dosages utilized for compounds of formula I are directly comparable on a molar basis with those dosages which have now been known in the art for the corresponding Vitamin $D_3$ metabolite for the same therapeutic indication. The compounds of formula I may be administered in pharmaceutical common unit dosage forms in conjunction with conventional pharmaceutical materials e.g. as compressed tablet, coated tablet, hard or soft elastic gelatin capsules, in propylene glycol solution, oil solution, aqueous suspension, and the like. Compounds of the present invention have an advantage over the parent Vitamin $D_3$ metabolites in that they form base salts which are water soluble and thus can be administered in the form of aqueous solutions either orally or parenterally. Suitable aqueous solutions can be prepared in a manner known per se utilizing sterile water, saline or buffered preparations. Preferred compounds of formula I for therapeutic or nutritional use are those where n=2, i.e the hemisuccinate derivatives. A most preferred compound of the invention is 1α,25-dihydroxycholecalciferol-3-hemisuccinate or its sodium salt.

The comounds of formula I of the present invention are also useful as haptens which can be used to prepare antigens which in turn can be injected into host animals to elicit antibodies which are immunologically reactive with the corresponding Vitamin $D_3$ metabolites. These antibodies are employed as reagents in immunoassays, i.e., radioimmunoassays, for said Vitamin $D_3$ metabolites. The utilization of the compounds of formula I as haptens is carried out by procedures now well known in the art. Such procedures, for example, are set forth in great detail in co-assigned U.S. patent application Ser. No. 867,204, filed Jan. 5, 1978 inventors Fairney et al, with respect to a 25-hemisuccinate derivative.

Such procedures involve, in summary, covalently coupling the hapten, through its free carboxyl group to an immunogenic carrier material, such as protein, preferably bovine serum albumin. The aforesaid coupling is conveniently carried out in aqueous media in the presence of a carbodimide such as 1-ethyl-3-(3-dimethylamino-propyl) carbodimide.

The resulting antigen is injected into a suitable host animal preferably using a conventional adjuvant material. Suitable animal hosts include mammals such as rabbits, horses, goats, guinea pigs, rats, cows, sheep and the like. Improved antibody titers can be obtained by repeated injections over a period of time. The antibodies are useful as reagents for the determination of the concentration of the corresponding Vitain $D_3$ metabolites in biological fluids, preferably plasma using assay procedures well known in the art.

When compounds of the invention contain 24,25-dihydroxy or 25,26-dihydroxy substituents, the preferred configuration are 24R and 25R respectively.

EXAMPLE 1

A solution of 3.2 g (7.68 mmol) of 1α,25-dihydroxy-7-dehydrocholesterol in 10 ml of anhydrous pyridine and 50 ml of anhydrous tetrahydrofuran was cooled at $-10°$ C. Under argon and within 30 min, a solution of 2.4 g (8.96 mmol) of succinic acid mono-2,2,2-tricholoroethylester chloride in 5 ml of anhydrous tetrahydrofuran was added and the obtained mixture stirred for 90 min at $-10°$ C. After this time, 10 ml of methanol were added, the mixture stirred 30 min and then the solvents evaporated in vacuo. The residue was dissolved in 200 ml of ethyl acetate and successively washed with 50 ml of 1 N hydrochloric acid, 3×50 ml of water, 50 ml of 2 N potassium bicarbonate solution and 3×50 ml of brine. Evaporation of the solvent gave 5.0 g of crude product. This was purified by column chromatography to give 2.75 g (55% yield) of pure 1α,25-dihydroxy-7-dehydrocholesterol-3-(2',2',2'-trichloroethylsuccinate). Crystallization from hexane-ethyl acetate gave white crystals, m.p. 93°–95° C. $[\alpha]_D^{25} = -14.73°$ (c=0.56, ethanol).

Anal. Calcd for $C_{33}H_{49}O_6Cl_3$: C, 61.16; H, 7.62; Cl, 16.41. Found: C, 61.02; H, 7.86; Cl, 16.33.

IR(KBr) 3400–3500 (m), 1758 (s), 1733 (s), 1650 (w), 1600 (w)cm$^{-1}$.

Mass Spectrum (70 eV) m/e (rel. intensity) 398 (90), 380 (100), 101 (80).

UV (ethanol): $\lambda_{max}(\epsilon)$ 251 (4100), 263 (7600), 271 (10,650), 282 (11,400), 294 (6700) nm.

EXAMPLE 2

A solution of 500 mg. (0.771 mmol) of 1α25-dihydroxy-7-dehydrocholesterol-3-(2',2',2'-trichloroethyl succinate) in 400 ml of n-hexane and 100 ml of tetrahydrofuran was irradiated with an ultraviolet lamp (Hanovia 450 W high pressure lamp) at 0° C. for 10 min. The solvents were evaporated in vacuo at room temperature and the components of the photolysis mixture separated by high pressure liquid chromatography, using a Waters Associates chromatograph (Model 244) and a 8 feet×⅜ inches Porasil A$^{(R)}$ column and hexane/ethyl acetate (1:1) as eluent, to give 111 mg of 1α,25-dihydroxyprecholecalciferol-3-(2',2',2'-trichloro ethyl succinate) as a thick oil and 197 mg of unreacted starting material.

NMR (CDCl$_3$) 0.70 (3H,s, CH$_3$-18), 1.21 (6H,s(CH$_3$)$_2$-C-25), 2.75 (4H, bs, CO CH$_2$ CH$_2$ CO),4.78(2H,s, CH$_2$ CCl$_3$),5.53(1H,bs, CH-9)5.86(2H,bs, CH-6 anol CH-7)ppm.

EXAMPLE 3

A solution of 692 mg (1.07 mmol) of the prechlolecalciferol obtained in Example 2 in 20 ml of anhydrous dioxane was refluxed under argon for 30 min. After cooling, the solvent was evaporated in vacuo and the residue purified by high pressure liquid chromatography, using a 4 feet×1 inch silica column (37–44μ particle size), eluted with hexane-ethyl acetate (2:1) to give 86 mg of unreacted starting material and 395 mg of pure 1α,25-dihydroxycholecalciferol 3-(2',2',2'-tricholoroethyl) succinate.$[\alpha]_D^{25} = -32.11$ (c=0.31, ethanol).

Anal. Calcd. for $C_{33}H_{49}Cl_3O_6$: C,61.16;H,7.62. Found: C,61.18; H,7.88.

IR (KBr): 3540-3360 (m), 1758 (s), 1735 (s), 1645 (w).

NMR (CDCl$_3$): δ 0.54 (s, 3H, CH$_3$-18), 0.93 (bol, 3H, J=5.0 Hz, CH$_3$-21) 1.21 (s, 6H, (CH$_3$)$_2$ C-25), 2.72 (AB quartett, 4H, J=4H$_2$, Δν=6H$_2$, CO CH$_2$ CH$_2$CO), 4.40 (bm, 1H, CH-1), 4.73 (s, 2H, CH$_2$ CCl$_3$), 5.03 and 5.35 (2bs, 1H each=CH$_2$-19), 6.00 and 6.34 (2d, 1H each J=12.0 Hz, CH-6 and CH-7)ppm Mass.Spectrum (70 ev): m/e (rel. intensity) 616 (9), 614 (10) 317 (48), 316 (100), 101 (77).

UV (ethanol): $\lambda_{max}(\epsilon)$ 210 (16,000), 263 (14550) nm.

EXAMPLE 4

A solution of 400 mg (0.617 mmol) of the cholecalciferol derivative obtained in Example 3 in a mixture of 50 ml of tetrahydrofuran and 30 ml of water was stirred at 0° C. with 10 g of zinc powder. Slowly, 10 ml of a 1 molar potassium phosphate monobasic was added and the resulting mixture stirred three hours under argon atmosphere. After this time, it was filtered, the residue washed with 30 ml of tetrahydrofuran and the filtrate evaporated in vacuo at room temperature to dryness. The residue was purified with a Waters Associates liquid chromatograph (Model 244) using a 4 feet × ⅜ inches phenylbondapak ® column and methanol-water (3:1) as eluent to give 310 mg (97% yield) of pure 1α,25-dihydroxycholecalciferol-3-hemisuccinate as white amorphous solid.

IR (KBR): 3480–3320 (m), 1735 (s), 1715 cm$^{-1}$.
NMR (CDCl$_3$): δ 0.54 (s, 3H, CH$_3$-18), 0.92 (bd, 3H, J=5.5 Hz, CH$_3$-21), 1.22 (s, 6H, (CH$_3$)$_2$ C-25), 2.62 (s, 4H, COCH$_2$CH$_2$CO), 4.40 (bs, 1H, CH-1), 5.00 and 5.33 (2bs, 1H each, =CH$_2$-19) 5.20 (bm, 1H, CH-3), 6.00 and 6.32 (2d, 1H each, J=12.0 Hz, CH-6 and CH-7)ppm.

Mass. Spectrum (70 eV): m/e (rel. intensity) 498 (13), 398 (15), 330 (91), 105 (63), 59 (100).

UV (ethanol): $\lambda_{max}(\epsilon)$ 211 (12300), 264 (12700) nm.

EXAMPLE 5

A mixture of 2.0 g (4.38 mmol) of 24R,25-dihydroxycholecalciferol 24,25-acetonide and 0.5 g (5.00 mmol) of succinic anhydride in 5 ml of dry pyridine was heated at 100° C. under argon in the dark for 20 hrs. The solvent was evaporated in vacuo and the residue dissolved in ethyl acetate and washed with 1 N hydrochloric acid, then with brine until neutral. The organic phase was dried over anhydrous sodium sulfate, filtered and evaporated in vacuo. The residue was purified with a Waters Associates liquid chromatograph (Model 244) using a 4'× ⅜" Phenylbondapak ® column and methanol-water as eluent to give pure 24R,25-dihydroxycholecalciferol 24,25-acetonide 3-hemisuccinate.

EXAMPLE 6

In analogy to the procedure of Example 5, the following starting compounds are converted to the indicated desired hemisuccinates:

| Starting Compound | Product |
| --- | --- |
| 1α,24,25-trihydroxycholecalciferol 24,25 acetonide | 1α24,25-trihydroxycholecalciferol 24,25-acetonide 3-hemisuccinate |
| 25,26-dihydroxycholecalciferol 25,26-acetonide | 25,26-dihydroxycholecalciferol 25,26-acetonide 3-hemisuccinate |

EXAMPLE 7

A mixture of 0.500 g (0.898 mmol) of 24R,25-dihydroxycholecalciferol 24,25-acetonide 3-hemisuccinate in 10 ml of methanol and 1.0 g of the hydrogen form of all ionic exchange resin (AG 50W-XA from Bio-Rad Laboratories, 200–400 mesh) was stirred at room temperature under argon and in the dark for 2 days. The reaction mixture was filtered, the resin washed with 10 ml of methanol and the combined filtrates evaporated the vacuo. The residue was purified with a Waters Associates liquid chromatograph (Model 244) using a 4'× ⅜" Phenylbondapak ® column and methanol-water as eluent to give pure 24R,25-dihydroxycholecalciferol 3-hemisuccinate.

EXAMPLE 8

In analogy to the procedure of Example 7, the following starting compounds are converted to the indicated desired end products.

| Starting Compound | Product |
| --- | --- |
| 1α,24,25-trihydroxycholecalciferol 24,25-acetonide 3-hemisuccinate | 1α,24,25-trihydroxycholecalcifero 3-hemisuccinate |
| 25,26-dihydrocholecalciferol 25,26-acetonide 3-hemisuccinate | 25,26-dihydroxycholecalciferol 3-hemisuccinate |

EXAMPLE 9

The bilogical activities of 1α,25-dihydroxycholecalciferol-3-hemisuccinate and sodium 1α,25-dihydroxycholecalciferol were compared to the corresponding Vitamin D$_3$ metabolite, i.e., 1α,25-dihydroxycholecalciferol (calcitriol) in two animal models.

The first assay is the chick assay involving 21 days of subcutaneous administration to chicks fed a vitamin D-deficient diet. Specific details of this assay have been published by Boris et al., J. Nutrition 107, 194 (1977).

The second assay is the disphosphonate rat assay wherein rats are treated for ten days concurrently with subcutaneous administration of test compound and diphosphonate. This assay is described by Boris et al, J. Nutrition, 108, 1899 (1978).

Results obtained in these assays are summarized in Tables 1 and 2 below:

Table 1

| | Chick Assay | | |
| --- | --- | --- | --- |
| | Mean Tibia Ash (mg) ± S.E. | | |
| Dose/Day, s.c. picomoles/chick | Calcitriol | 3-Hemisuccinate* | Difference |
| 2.4 | 121.8 ± 6.8 | 111.0 ± 4.3 | NS |
| 7.2 | 129.5 ± 6.0 | 117.2 ± 4.0 | NS |
| 24.0 | 170.9 ± 7.3 | 169.7 ± 6.5 | NS |
| 72.1 | 192.8 ± 11.5 | 224.2 ± 11.8 | NS |

Both compounds administered in propylene glycol.
5–10 chicks per group. 21 days treatment.
*1α,25-dihydroxycholecalciferol-3 hemisuccinate.

| | Mean Tibia Ash (mg) ± S.E. | | |
| --- | --- | --- | --- |
| Dose/Day, s.c. picomoles/chick | Calcitriol | 3-HS, Sodium* | Difference |
| 0 | 105.4 ± 4.4 | 95.5 ± 4.3 | NS |
| 2.4 | 111.2 ± 7.4 | 113.7 ± 5.8 | NS |
| 7.2 | 120.5 ± 6.7 | 107.1 ± 4.5 | NS |
| 24.0 | 161.2 ± 6.1 | 123.6 ± 7.1 | p .001 |
| 72.1 | 228.2 ± 8.9 | 193.9 ± 6.5 | p .01 |

Calcitriol in propylene glycol. 3 HS, Sodium in water.
7–10 chicks per group. 21 days treatment.
*sodium 1α,25-dihydroxycholecalciferol-3-hemisuccinate.

Table 2

| | Diphosphonate Rat Assay | | |
| --- | --- | --- | --- |
| | Tibial Epiphyseal Plate (μ) | | |
| Dose/Day, s.c. picomoles/rat | Calcitriol | 3-Hemisuccinate | Difference |
| 0 | | 1296 ± 19 | |
| 7.2 | 946 ± 21 | 1202 ± 14 | p .001 |
| 14.4 | 752 ± 17 | 804 ± 11 | p .05 |
| 28.8 | 661 ± 8 | 693 ± 23 | NS |
| 57.7 | 437 ± 6 | 598 ± 14 | p .001 |

Both compounds administered in propylene glycol.
9–10 rats per group. 10 days treatment.

Table 2-continued

| Dose/Day, s,c. picomoles/rat | Tibial Epiphyseal Plate ($\mu$) | | |
|---|---|---|---|
| | Calcitriol | 3-HS, Sodium | Difference |
| 0 | 1048 ± 61 | | |
| 7.2 | 1169 ± 61 | 1100 ± 73 | NS |
| 14.4 | 1035 ± 59 | 1044 ± 75 | NS |
| 28.8 | 740 ± 44 | 928 ± 65 | p .05 |
| 57.7 | 450 ± 7 | 491 ± 30 | NS |

Calcitriol in propylene glycol. 3-HS, Sodium in water.
10 rats per group. 10 days treatment.

In chicks, there was no significant difference between calcitriol and its 3-hemisuccinate when given subcutaneously in the same vehicle at equimolar doses. The 3-hemisuccinate sodium salt was slighly less potent than calcitriol when the salt was given in water and compared to calcitriol in propylene glycol at equimolar doses at equimolar doses.

In diphosphonate-treated rats the 3-hemisuccinate was slightly less potent than calcitriol, while the 3-hemisuccinate sodium salt was equipotent to calcitriol.

These results, obtained in two different animal models and utilizing two different species, indicate that calcitriol and its water soluble 3-hemisuccinate sodium salt are, for practical purposes, biologically equivalent.

EXAMPLE 10

The following parenteral formulation was made:

| Ingredients | per ml | per liter |
|---|---|---|
| 1α,25-dihydroxycholecalciferol 3-hemisuccinate | 3.75 mcg | 3.72 mg |
| Benzyl alcohol | 0.01 ml | 10 ml |
| Ammonium acetate | 2 mg | 2 g |
| Sodium chloride | 8.5 mg | 8.5 g |
| Sodium metabisulfite | 2 mg | 2 g |
| Disodium edetate | 0.1 mg | 100 mg |
| Water for Injection q.s. | 1 ml | 1 liter |
| Initial pH-5.59, Final pH-7.01 (after adjustment) | | |

Note:
This preparation contains the equivalent of 2.5 mcg/ml of 1,25-dihydroxy D$_3$ with a 20% manufacturing excess to allow for reasonable stability.

Note that by adjusing the pH of the preparation to 7 with sodium hydroxide, the sodium salt is prepared in situ, buffered by ammonium acetate. The benzyl alcohol is present as an antimicrobial preservative, with sodium chloride to render the preparation isotonic, sodium metabisulfite as an aqueous soluble antioxidant, and the disodium edetate as a metal chelating agent to aid in stabilizing the preparation.

The formulation was sterilized by bacteriological filtration through a suitable filter (Selas candle or Millipore membrane) and aseptically filled into sterile 1 ml ampuls.

We claim:

1. A compound of the formula

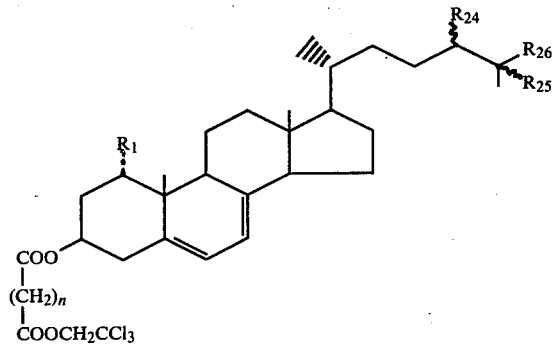

where $R_1$, $R_{24}$, $R_{25}$ and $R_{26}$ each independently are hydrogen hydroxy, or fluorine provided that at least one of $R_1$-$R_{24}$, $R_{25}$ and $R_{26}$ is hydroxy or fluorine, any two of $R_{24}$, $R_{25}$ and $R_{26}$ taken together are hydroxys protected as the acetonide, and n is an integer selected from 2 or 3.

2. The compound of claim 1 which is 1α,25-dihydroxy-7-dehydrocholesterol-3-(2',2',2'-trichloroethylsuccinate).

3. A compound of the formula

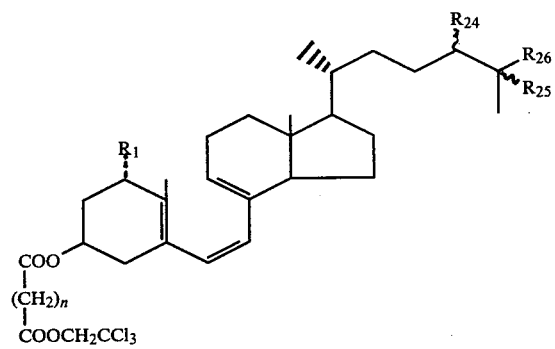

where $R_1$, $R_{24}$, $R_{25}$ and $R_{26}$ each independently are hydrogen hydroxy, or fluorine provided that at least one of $R_1$-$R_{24}$, $R_{25}$ and $R_{26}$ is hydroxy or fluorine, any two of $R_{24}$, $R_{25}$ and $R_{26}$ taken together are hydroxys protected as the acetonide, and n is an integer selected from 2 or 3.

4. The compound of claim 3 which is 1α,25-dihydroxyprecholecalciferol-3-(2',2',2'-trichloroethyl)succinate).

5. A compound of the formula

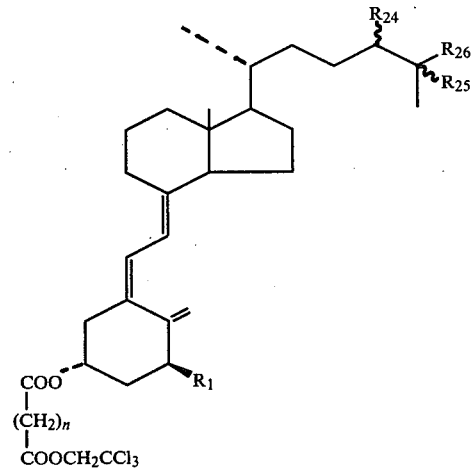

where $R_1$, $R_{24}$, $R_{25}$ and $R_{26}$ each independently are hydrogen hydroxy or fluorine, provided that at least one of $R_1$, $R_{24}$, $R_{25}$ and $R_{26}$ is hydroxy or fluorine, any two of $R_{24}$, $R_{25}$ and $R_{26}$ taken together are hydroxys protected as the acetonide, and n is an integer selected from 2 or 3.

6. The compound of claim 5 which is 1α,25-dihydroxycholecalciferol-3-(2',2',2'-trichloroethyl) succinate.

* * * * *